(12) United States Patent (10) Patent No.: US 12,691,190 B2

Bernstein (45) Date of Patent: Jul. 28, 2026

(54) STERILIZING COVER FOR TOUCHSCREENS COMPRISING UV EMITTING SOURCE

(71) Applicant: Eric F. Bernstein, Gladwyne, PA (US)

(72) Inventor: Eric F. Bernstein, Gladwyne, PA (US)

(73) Assignee: Phase Shield, LLC, Dover, DE (US)

( * ) Notice: Subject to any disclaimer, the term of this patent is extended or adjusted under 35 U.S.C. 154(b) by 494 days.

(21) Appl. No.: 17/224,453

(22) Filed: Apr. 7, 2021

(65) Prior Publication Data

US 2021/0308304 A1 Oct. 7, 2021

Related U.S. Application Data

(60) Provisional application No. 63/006,436, filed on Apr. 7, 2020.

(51) Int. Cl.
| | |
|---|---|
| *A61L 2/10* | (2026.01) |
| *A61L 2/084* | (2026.01) |
| *A61L 2/085* | (2026.01) |

(52) U.S. Cl.
CPC .................. *A61L 2/10* (2013.01); *A61L 2/084* (2013.01); *A61L 2/085* (2013.01); *A61L 2202/11* (2013.01)

(58) Field of Classification Search
CPC . A61L 2/10; A61L 2/084; A61L 2/085; A61L 2202/11; C09K 11/77; C09K 11/7777; G06F 3/0393
See application file for complete search history.

(56) References Cited

U.S. PATENT DOCUMENTS

| | | | |
|---|---|---|---|
| 10,596,281 B1* | 3/2020 | Tchon | .................... H05B 47/16 |
| 2009/0130169 A1* | 5/2009 | Bernstein | ........... C09K 11/7789 |
| | | | 427/430.1 |
| 2019/0336626 A1* | 11/2019 | Maa | ......................... A61L 2/088 |
| 2021/0215857 A1* | 7/2021 | Nichol | ................. G02B 5/0257 |
| 2022/0268984 A1* | 8/2022 | Nichol | ................. G02B 6/0028 |

* cited by examiner

*Primary Examiner* — Regina M Yoo
(74) *Attorney, Agent, or Firm* — Finnegan, Henderson, Farabow, Garrett & Dunner LLP

(57) ABSTRACT

A touchscreen cover comprising a top side facing the user of a touchscreen, a bottom side facing the touchscreen and at least one UV emitting device or material for emitting energy having a wavelength ranging from 100-400 nm, that is in optical communication with the top side. A method of sterilizing a touchscreen by exposing a touchscreen cover to UV radiation for a time sufficient to deactivate or kill at least one microorganism found on the touchscreen. A method of coating a cover for touchscreen with a sterilizing composition is also disclosed.

14 Claims, No Drawings

STERILIZING COVER FOR TOUCHSCREENS COMPRISING UV EMITTING SOURCE

PRIORITY

This application claims the benefit of priority to U.S. Provisional Application No. 63/006,436, filed Apr. 7, 2020, which is incorporated herein by reference in its entirety.

FIELD OF USE

The present disclosure generally relates to a sterilizing cover for touchscreens that directs UV energy, such as UVB and/or UVC to the surface of the touchscreen. The present disclosure also relates to sterilizing covers that contain devices for generating germicidal UV energy, such as comprising organic and/or inorganic phosphors that convert an incident radiation to a different radiation, or combinations thereof. The present disclosure also relates to methods of sterilizing the surface of a touchscreen by elimination, inactivation or reduction of pathogens including viruses, bacteria, fungi, yeast or prions.

BACKGROUND

Touchscreen technology was first described in the 1960's. By 1975 the U.S. Patent Office issued one of the first patents, U.S. Pat. No. 3,911,215 on a resistive touchscreen to Hurst et al. Since that time, touchscreens have become common in a variety of electronic devices such as smart phones, tablets, personal computers, point-of-sale (POS) systems, kiosks, digital appliances, and other functional electronics, including automated teller machines (ATMs).

The ubiquitous use of touchscreens necessarily requires increased human-computer interaction particularly public-use touchscreens, such as self-check in kiosks at airports and train stations to self-check out stations at grocery stores. Even if public touchscreens are wiped down frequently throughout the day cleaning, harmful bacteria can remain on touchscreen surfaces for days.

As touchscreen technology becomes a more integral part of our daily lives, our exposure to germs increases as these surfaces are touched by countless people every day, each time collecting germs and bacteria from users, such as *Staphylococcus* (staph), and *Enterococcus faecalis* (*E. faecalis*) which is notorious for causing hospital-acquired infections (HAIs). A majority of the germs found on touchscreen surfaces in public areas is likely the result of poor hand hygiene. Studies have shown that about 34% of Americans do not wash their hands after using the restroom. This might explain the results of research done by Insurance Quotes which indicates the average airport self-check-in screen at contained 253,857 colony-forming unit (CFU). In comparison, on average only 172 CFU are found on public toilet seats.

In view of the foregoing, there is a need to be able to continuously and automatically sterilize the surface of touchscreens. It is known that UV-C light is "germicidal" because it can deactivate the DNA of bacteria, viruses and other pathogens and thus destroys their ability to multiply and cause disease without the need for heat or chemicals. The short wavelength associated with UVC energy, specifically between about 250 to about 260 nm, and lower, provides the highest germicidal effectiveness, and thus is lethal to a variety or microorganisms, including the most common molds, virus, and bacteria, such as *Salmonella*,

*Staphylococcus, Streptococcus, Legionella, Bacillus*, dysentery, infectious hepatitis, influenza, coronavirus and rotavirus. Accordingly, there is a need for a more economical and safer method of using the powerful germicidal effects of UV technology.

To solve at least one of the foregoing problems, there is described a touchscreen cover that contains at least one mechanism for generating UV energy, such as UVB and/or UVC energy on the surface of the touchscreen. To that end, there is described a cover for touchscreens, such as a plastic or glass cover, that directs UVC on the user facing surface of a touchscreen. In one embodiment, UVC energy is generated from the up-conversion of inherent blue light emitted from the touchscreen device itself by organic or inorganic phosphors contained in the cover.

SUMMARY OF INVENTION

Thus, the present disclosure is directed to a composition for converting electromagnetic energy to ultraviolet radiation or electromagnetic radiation of shorter wavelengths for the purpose of sterilization by elimination, inactivation or reduction of pathogens including viruses, bacteria, fungi, yeast or prions.

In one embodiment, there is disclosed a touchscreen cover, comprising: a top side facing the user of a touchscreen, and a bottom side facing the touchscreen, wherein the cover is substantially transparent and adapted to substantially cover the touchscreen. In an embodiment, the cover has a thickness that allows user inputs to be transmitted to the touchscreen, wherein the cover comprises a UV emitter, such as a composition for converting electromagnetic energy to UV radiation or electromagnetic radiation of a shorter wavelength, or a device for emitting UV energy, such as a diode.

In an embodiment, the composition comprises: at least one phosphor capable of converting an initial electromagnetic energy (A) to a different electromagnetic energy (B), said different electromagnetic energy (B) comprising UVB, UVC, or combinations thereof.

There is also disclosed a method of sterilizing a touchscreen that is connected to an electronic device, by exposing it to radiation of a shorter wavelength, such as UV radiation. In an embodiment, the method comprises: exposing a cover located on a touchscreen to an incident light comprising ultraviolet, visible or infrared light, wherein the cover comprises a UV emitter, such as a composition comprising at least one phosphor capable of converting the visible or infrared light to UV radiation or radiation of a shorter wavelength. In an embodiment, the UV emitter is a device, such as a diode that generates UV radiation. In an embodiment, the exposing step is performed for a time sufficient to deactivate or kill at least one microorganism chosen from bacteria, virus, mold, protozoa, and yeast.

There is also disclosed a method of coating a cover for touchscreen with a sterilizing composition, the method comprises: spraying, dipping, or painting onto said article, a composition comprising, in an organic or inorganic media, at least one phosphor capable of converting said UVB, UVA, visible or infrared light to UVC radiation or radiation of shorter wavelength.

DETAILED DESCRIPTION OF THE INVENTION

Definitions

Certain terms used herein are defined below:

"Up-converting" refers to the ability to convert electromagnetic energy to a higher energy or shorter wavelength.

"Down-converting" refers to the ability to convert electromagnetic energy to a lower energy or longer wavelength.

"At least one" as used herein means one or more and thus includes individual components as well as mixtures/combinations.

A "film," as used herein, refers to a continuous coating, i.e., a coating without holes visible to the naked eye, which covers at least a portion of the substrate to which the composition was applied. Further, a film, as used herein, may have any thickness and is not restricted to a thin coating.

"Film-forming polymer" as used herein means a polymer which, by itself or in the presence of a film-forming auxiliary, is capable, after dissolution in at least one solvent, of forming a film on the substrate to which it is applied once the at least one solvent evaporates.

"Polymers" as defined herein comprise copolymers (including terpolymers) and homopolymers, including but not limited to, for example, block polymers, cross linked polymers, and graft polymers.

"UV radiation" as defined herein encompasses radiation having a wavelength ranging from 100-400 nm, specifically including UVC (200-290 nm), UVB (290-320 nm) and UVA (320-400 nm) radiations.

"UV emitter" as defined herein includes a material or device for generating UV radiation. Non-limiting examples of materials for emitting UV radiation include at least one phosphor described herein capable of converting an initial electromagnetic energy (A) to a UV energy. Non-limiting examples of a device for emitting UV radiation include UV generating diodes, such as a or liquid crystal diode (LCD) or a light emitting diode (LED).

"Optical communication" means light is able to be transmitted from a light emitting source to another location, such as the surface of a cover. Optical communication does not require physical, electrical or thermal contact.

It is to be understood that both the foregoing general description and the following detailed description are exemplary and explanatory only and are not restrictive of the invention, as claimed. Reference will now be made in detail to exemplary embodiments of the present invention.

Ultraviolet (UV) radiation is known as a highly effective means of destroying microorganisms. For example, typical UV radiation that can be used in the described devices include UVC (200-290 nm), UVB (290-320 nm) and UVA 320-400 nm. In one embodiment, the desired wavelength would range from 240 nm to 260 nm, such as 254 nm. It is known that this range is highly effective in killing bacteria, molds, protozoa, yeasts, and viruses on surfaces, such as touchscreens. Methods of killing the pathogen from exposure to UVC include fatal harm to microbial DNA by triggering adjacent thymine molecules to dimerize, thereby disrupting DNA and RNA replication.

As described herein, there are multiple ways to sterilize the surface of a touchscreen with UV energy. In one embodiment, there is described a cover for a touchscreen comprising a UV emitter. In one embodiment, the UV emitter is a material, such as a phosphor that converts an initial incident radiation to UV radiation.

A phosphor is a substance that exhibits the phenomenon of phosphorescence, or a sustained glowing after exposure to light or energized particles such as electrons. Phosphors have a finite emission time, with persistence being inversely proportional to wavelength. Because the persistence of the phosphor increases as the wavelength decreases, it is known that red and orange phosphors do not have sufficiently long glow times.

The organic and inorganic phosphors used in the present invention differ from these traditional phosphors in that they have an indefinite glow time. In addition, they have the ability to transfer electromagnetic energy of one frequency to a higher frequency (referred to as "up-converting") or to a lower frequency (referred to as "down-converting"), depending on the rare earth metal used. A description of such phosphors is provided U.S. Pat. No. 5,698,397, which is herein incorporated by reference. This patent describes the use of such phosphors for biological and other assays.

Up-converting crystals, which take light or electromagnetic radiation of one frequency and convert it to light of a higher frequency (thus shorter wavelength), appear to contradict a basic law of physics directed to conservation of energy. However, two, four or more photons of a lower frequency or longer wavelength are converted into a single photon of higher frequency or shorter wavelength. Thus, a number of photons of lower energy combine to produce one photon of higher energy. These compounds can emit visible light when irradiated with infrared light.

In contrast, down-converting crystals take light or electromagnetic radiation of one frequency and convert it to light of a lower frequency (thus longer wavelength). These compounds can emit red or IR light when irradiated with UV or visible light.

Phosphors are usually made from a suitable host material, to which an activator is added. Suitable activators that may be used in the present invention include ytterbium, erbium, thulium, holmium, and combinations of these materials. Non-limiting examples of activator couples include ytterbium/erbium, ytterbium/thulium, and ytterbium/holmium.

Generally, host materials comprise oxides, halides, sulfides, and selenides of various rare earth metals. Suitable phosphor host materials that may be used in one embodiment of the present invention include gadolinium, yttrium, lanthanum, and combinations of these materials. Particular non-limiting embodiments of such crystal matrices which may comprise the host material include oxy-sulfides, oxy-fluorides, oxychlorides, or vanadates of various rare earth metals.

Non-limiting embodiments of the organic and/or inorganic phosphors that can be used as host materials in the present disclosure include sodium yttrium fluoride ($NaYF_4$), lanthanum fluoride ($LaF_3$), lanthanum oxysulfide ($La_2O_2S$), yttrium oxysulfide ($Y_2O_2S$), yttrium fluoride ($YF_3$), yttrium gallate, yttrium aluminum garnet (YAG), gadolinium fluoride ($GdF_3$), barium yttrium fluoride ($BaYF_5$, $BaY_2F_8$), gadolinium oxysulfide ($Gd_2O_2S$), calcium tungstate ($CaWO_4$), yttrium oxide:terbium ($Yt_2O_3Tb$), gadolinium oxysulphide:europium ($Gd_2O_2S$:Eu); lanthanam oxysulphide:europium ($La_2O_2S$:Eu); and gadolinium oxysulphide: promethium, cerium, fluorine ($Gd_2O_2S$:Pr,Ce,F); and generally ($YLuScA)PO_4$, wherein A is an activator selected from the group of bismuth, praseodymium and neodymium.

Other phosphors which may be used in the present composition, along with their characteristic absorption colors (and wavelengths) include, are not limited to: $Gd_2O_2S$:Tb (P43), green (peak at 545 nm); $Gd2O_2S$:Eu, red (627 nm); $Gd_2O_2S$:Pr, green (513 nm); $Gd_2O_2S$:Pr,Ce,F, green (513 nm); $Y_2O_2S$:Tb (P45), white (545 nm); $Y_2O_2S$:Tb red (627 nm); $Y_2O_2S$:Tb, white (513 nm); Zn(0.5)Cd(0.4)S:Ag green (560 nm); Zn(0.4)Cd(0.6)S:Ag (HSr), red (630 nm); $CdWO_4$, blue (475 nm); $CaWO_4$, blue (410 nm); $MgWO_4$, white (500 nm); $Y_2SiO_5$:Ce (P47), blue (400 nm); $YAlO_3$:Ce (YAP), blue (370 nm); $Y_3Al_5O_{12}$:Ce (YAG), green (550 nm); $Y_3(Al,Ga)_5O_{12}$:Ce (YGG), green (530 nm); CdS:In, green (525 nm); ZnO:Ga, blue (390 nm); ZnO:Zn (P15), blue (495 nm); (Zn,Cd)S:Cu,Al (P22G), green (565 nm); ZnS:Cu,Al,Au (P22G), green (540 nm); ZnCdS:Ag,Cu (P20), green (530 nm); ZnS:Ag (P11), blue (455 nm); $Zn_2SiO_4$:Mn (P1), green (530 nm); ZnS:Cu (GS), green (520 nm); and the following crystals that emit in a UV-C range, e.g., from 200 to 280 nm, such as from 225 to 275 nm; $YPO_4$:Nd; $LaPO_4$:Pr; $(Ca,Mg)SO_4$:Pb; $YBO_3$:Pr; $Y_2SiO_5$: Pr; $Y_2Si_2O_7$:Pr; $SrLi_2SiO_4$:Pr,Na; and $CaLi_2SiO_4$:Pr.

In one embodiment, the organic and/or inorganic phosphors are present in the disclosed composition in an amount effective to convert electromagnetic radiation of a frequency (A) to a higher frequency (B). While in theory, the up-converting crystals of this embodiment can convert any electromagnetic energy to a higher energy (or shorter wavelength), in one embodiment, the electromagnetic radiation of frequency (A) comprises infrared or visible light, and the frequency (B) comprises ultraviolet (UV) radiation chosen from UVA, UVB, and UVC.

The organic and/or inorganic phosphors may be present in the disclosed composition in an amount ranging from 0.01% to 60% by weight, relative to the total weight of the composition, such as from 0.1% to 30% or even 1% to 15% by weight, relative to the total weight of the composition.

In one embodiment, the disclosed composition may further comprise an activator for the organic and/or inorganic phosphors, such as a ytterbium containing activator. Non-limiting examples of the ytterbium containing activator include ytterbium/erbium, ytterbium/thulium, ytterbium/terbium, and ytterbium/holmium.

The organic and/or inorganic phosphors according to the present disclosure typically have an average particle size ranging from 1 nm to 1 cm, such as from 1 nm to 1 mm, from 2 nm to 1000 nm, from 5-100 nm, or even 10-50 nm. The concentration of the organic and/or inorganic phosphors in the inventive composition as well as in the above-defined regions and the size of the organic and/or inorganic phosphors can be measured by methods known for such which are well known in the art. For example, x-ray diffraction (XRD), scanning electron microscopy (SEM), transmission electron microscopy (TEM), and/or BET surface area analysis may be used.

The organic and/or inorganic phosphors according to the present disclosure are typically synthesized from rare-earth doped phosphorescent oxide particles having the previously described sizes. The method further provides for homogeneous ion distribution through high temperature atomic diffusion.

A solid-phase precursor composition (hereinafter referred to as "the precursor composition") is prepared by mixing one or more rare earth element dopant precursor powders with one or more oxide-forming host metal powders. Stoichiometric amounts of host metal and rare earth element are employed to provide rare earth element doping concentrations in the final particle of at least 0.5 mol % up to the quenching limit concentration.

In one embodiment, the quenching limit concentration is about 15-18 mol % for europium-doped $Y_2O_3$ nanoparticles, while it is about 10 mol % for erbium-doped $Y_2O_3$ nanoparticles. Also, for Yb and Er-codoped $Y_2O_3$ nanoparticles, the quenching limit depends upon the ratio of Yb:Er.

The rare earth element dopant precursor powders include, but are not limited to organometallic rare earth complexes having the structure:

$$RE(X)_3$$

wherein X is a trifunctional ligand and RE is a rare earth element. Any rare earth element or combinations thereof can be used (i.e., europium, cerium, terbium, dysprosium, holmium, erbium, thulium, ytterbium, lutetium) with particular mention being made to europium, cerium, terbium, holmium, erbium, thulium and ytterbium, as well as the following combinations: ytterbium and erbium, ytterbium and holmium and ytterbium and thulium.

Strontium can also be used, and for purposes of the present invention, rare earth elements are defined as including strontium, are earth element dopant precursor powders include $Yb(TMHD)_3$, $Er(TMHD)_3$, $Ho(TMHD)_3$, $Tm(TMHD)_3$, erbium isopropoxide $(C_9H_{21}O_3Er)$, ytterbium isopropoxide $(C_9H_{21}O_3Yb)$, and holmium isopropoxide $(C_9H_{21}O_3Ho)$.

Examples of trifunctional ligands include tetramethylheptanedionate (TMHD), isopropoxide (IP), and the like.

The oxide forming host metal can be, but is not limited to, lanthanum, yttrium, lead, zinc, cadmium, and any of the Group II metals such as, beryllium, magnesium, calcium, strontium, barium, aluminum, radium and any mixtures thereof or a metalloid selected from silicon, germanium and II-IV semi-conductor compounds. Oxide-forming host metal powders include $Y(TMHD)_3$, $Al(TMHD)_3$, $Zr(TMHD)_3$, $Y(IP)$, and $Ti(IP)$.

The rare earth element dopant precursor powder and oxide-forming host metal powders are mixed to form the precursor composition, and vaporized. An inert carrier gas, such as, but not limited to, nitrogen, argon, helium, and mixtures thereof, transports the vaporized precursor composition to a low pressure combustion chamber that houses a flame.

The flame produces active atomic oxygen via chain-initiation reaction of $$H + O_2 = OH + O \tag{i}$$

A high concentration of oxygen in the flame activates and accelerates the oxidation of rare-earth ions and host materials through a series of reactions:

$$R + O \rightarrow RO; \tag{ii}$$

$$RO + O \rightarrow ORO; \text{ and} \tag{iii}$$

$$ORO + RO \rightarrow R_2O_3 \tag{iv}$$

Reactions (ii) through (iv) are much faster than the oxidation reaction in low temperature processing represented by the reaction below;

$$2R + 3/2O_2 = R_2O_3 \tag{v}$$

The reaction represented by formula (v) has a much higher energy barrier than the reactions in formulae (i)-(iv) in which radicals formed in flames diffuse and help produce faster ion incorporation.

Generally, in flame spray pyrolysis a higher flame temperature increases particle sintering and agglomeration. However, in one embodiment of the present invention, spherical, discrete particles are formed. It is proposed that in addition to residence time, the initial size of the vapor-phase particles in the vaporized precursor composition and the precursor itself are the dominant factors that determine final particle size. As the vaporized precursor composition passes through the flame, it directly reacts and releases heat to the flame increasing flame temperature. Thus, a shorter flame residence time is needed, which allows for the production of smaller particles.

Temperatures ranging from about 1800 to about 2900° C. are used in one embodiment, with temperatures ranging from about 2200 to about 2400° C. being particularly noted. Temperatures within this range produce monodispersed rare earth doped activated oxide nanoparticles without significant agglomeration having an essentially uniform distribution of rare earth ions within the particles. Actual residence time will depend upon reactor configuration and volume, as well as the volume per unit time of vaporized precursor composition delivered at a given flame temperature. Cubic phase particles are obtained having an average particle size ranging from 5 to 50 nanometers, such as from 10 to 20 nanometers. Until recently, it was not possible to obtain activated cubic phase particles on a nanoscale. The particles also exhibit quenching limit concentrations heretofore unobtained.

The flame temperature can be manipulated by adjusting the flow rates of the gas(es). For example, the temperature of the flame can be increased by increasing the methane flow rate in a methane/oxygen gas mixture. Guided by the present specification, one of ordinary skill in the art will understand without undue experimentation how to adjust the respective flow rates of reactive gas(es) and inert carrier gas to achieve the flame temperature producing the residence time required to obtain an activated particle with a predetermined particle size.

Any reactive gas can be used singularly or in combination to generate the flame for reacting with the vaporized precursor composition, such as, but not limited to, hydrogen, methane, ethane, propane, ethylene, acetylene, propylene, butylenes, nbutane, iso-butane, n-butene, iso-butene, n-pentane, iso-pentane, propene, carbon monoxide, other hydrocarbon fuels, hydrogen sulfide, sulfur dioxide, ammonia, and the like, and mixtures thereof.

A hydrogen flame can produce high purity nano-phosphors without hydrocarbon and other material contamination. In the depicted embodiments, the flame length determines particle residence time within the flame. Higher temperatures produce satisfactory nanoparticles with shorter flames. Flame length is similarly manipulated by varying gas flow rates, which is also well understood by the ordinarily skilled artisan. Increasing the flame length increases the residence time of the particles in the flame allowing more time for the particles to grow. The particle residence time can be controlled by varying the different flow rates of the gases and is readily understood by one of ordinary skill in the art guided by the present specification.

The compositions according to the invention further comprises at least one organic or inorganic media in or on which the disclosed phosphors are dispersed. In one embodiment, the organic media comprises a plastic resin, such as thermoplastic elastomers, high temperature plastics, and engineering thermoplastics. Non-limiting examples of such resins include a polymer or co-polymer of polyvinyl chloride (PVC), acrylonitrile butadiene styrene (ABS), olefin, polycarbonate, styrene, nylon, and acetal.

It is possible to obtain an intimate mixture of the described phosphors and resins by mixture them in a dry state and subsequently compounding them, which may be followed by forming them into desired shapes using known plastic forming techniques, such as injection molding.

The resins described herein are well-known to be formed into a variety of plastics, including clear covers and shields. When compounded in or coated on such a plastic material, it would be possible to achieve localized UVC treatment. The plastic composition used in such applications include polyvinyl chloride, polyolefin or polyester.

There is also disclosed an cover, such as a glass or plastic piece, for covering a touchscreen. For example, in one embodiment, there is disclosed a plastic piece for covering a touchscreen. In this embodiment, the device comprising the touchscreen is capable of emitting the longer wavelength radiation from the inherent backlighting of the device. This longer wavelength radiation will activate the crystals to create UV-C which impinges the surface of the touchscreen causing it to be disinfected. In one embodiment, the cover further comprises a coating on at least one of the interior or exterior walls that blocks the UV-C from exiting the plastic cover, thus preventing UVC from reaching a user of the touchscreen. In one embodiment, the coating for containing the UVC comprises a thin metal layer, or an oxide that is transparent or translucent to the initial energy A but that prevent UVC from exiting the cover, such as MgO, $TiO_2$, $SiO_2$ and $Al_2O_3$.

In another embodiment, the UV emitter is a device that generates UV radiation such as diode, including a light emitting diode (LED) or a liquid crystal diode (LCD). These types of diodes have several advantages that make them particularly useful for covers in touchscreen devices, including improved durability, and flexibility that allows them to fit into touchscreens, efficiency of power usage.

In one embodiment, there is described a cover for sterilizing a touchscreen, the cover comprising at least one LED module that is coupled to a cover for a touchscreen, such that a UV-emitting surface is in optical communication with a surface of the touchscreen cover that faces the user. In an embodiment, the LED module is included or embedded in the borders, edges, and/or boundaries of the touchscreen cover by at least one sealing layer.

In an embodiment, the sealing layer may comprise a UV reflective material, such that any light back-reflected from the light-emitting surface of the LED module may be at least partially conserved by re-reflection in the direction of the light emitting surface. In one non-limiting embodiment, the sealing layer may comprise a UV resistant organic material, silicone or silicone composites, a fluoropolymer or its composites. The sealing layer may for example be applied by dispensing or transfer molding, although it will be clear to the skilled person that other application techniques may also be used.

Translucent window element may, by way of non-limiting example, be composed of Polycrystalline Alumina (PC A) materials, such as for example Spinel ($MgAl_2O_4$), AION, or sapphire. However, other suitable translucent ceramic materials may also be used.

In one embodiment, the at least one LED module may be coupled with the translucent widow element such the LED is embedded within the body of the window element. In this embodiment, the light-emitting top surface of the LED is in direct physical contact with surfaces of the translucent window element. As a result, light exiting the top surface of the LED may be transmitted directly to the corresponding engaging surface of the window element, without propagating through any intermediary or interstitial layers.

In one embodiment, the LED module is coupled to the translucent window and not embedded therein. For example, the LED module and the translucent window are solidly adhered with an adhesive layer.

It is envisioned that touchscreens covered with the disclosed cover can undergo almost continuous germicidal treatment just by nature of it being exposed to visible light, whether ambient or for artificial.

There is also disclosed a method of sterilizing a touchscreen by exposing it to UVC radiation or radiation of a shorter wavelength, the method comprising: exposing to long-wave ultraviolet, visible or infrared light, a composition comprising, in an organic or inorganic media, at least one phosphor capable of converting said visible or infrared light to UVC radiation or radiation of a shorter wavelength, such as x-ray or gamma rays. In this embodiment, exposing is performed for a time sufficient to deactivate or kill at least one microorganism, including those chosen from bacteria, virus, mold, protozoa, and yeast.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and in the attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. The following examples are intended to illustrate the invention without limiting the scope as a result. The percentages are given on a weight basis.

What is claimed is:

1. A touchscreen cover, comprising: a top side facing the user of a touchscreen; a bottom side facing the touchscreen; and at least one material for emitting energy having a wavelength ranging from 100-400 nm, that is in optical communication with the top side, wherein the touchscreen cover is substantially transparent and adapted to substantially cover the touchscreen, the touchscreen cover having a thickness that allows user inputs to be transmitted to said touchscreen, wherein the at least one material for emitting energy having a wavelength ranging from 100-400 nm comprises a glass or plastic resin and at least one phosphor which is embedded in, or coated on the glass or plastic resin, wherein said at least one phosphor is configured to convert an initial electromagnetic energy (A) that is emitted from the touchscreen itself to a different electromagnetic energy (B), said different electromagnetic energy (B) comprising UVB, UVC, or combinations thereof.

2. The touchscreen cover of claim 1, wherein said at least one phosphor is chosen from sodium yttrium fluoride (NaYF4), lanthanum fluoride (LaF3), lanthanum oxysulfide (La2O2S), yttrium oxysulfide (Y2O2S), yttrium fluoride (YF3), yttrium gallate, yttrium aluminum garnet (YAG), gadolinium fluoride (GdF3), barium yttrium fluoride (BaYF5, BaY2F8), gadolinium oxysulfide (Gd2O2S), calcium tungstate (CaWO4), yttrium oxide:terbium (Yt2O3Tb), gadolinium oxysulphide:europium (Gd2O2S:Eu); lanthanum oxysulphide:europium (La2O2S:Eu); and gadolinium oxysulphide:promethium, cerium, fluorine (Gd2O2S:Pr,Ce,F); YPO4:Nd; LaPO4:Pr; (Ca,Mg)SO4:Pb; YBO3:Pr; Y2SiO5:Pr; Y2Si2O7:Pr; SrLi2SiO4:Pr,Na; and CaLi2SiO4:Pr.

3. The touchscreen cover of claim 1, wherein said composition having at least one phosphor comprises a host lattice represented by the formula $(Y_{1-x-y-z},Lu_x,Sc_y,A_z)PO_4$, wherein $0 \leq x < 1$ and $0 < y \leq 1$ and $0 \leq z < 0.05$ and A is an activator.

4. The touchscreen cover of claim 3, wherein the activator comprises ytterbium, bismuth, praseodymium and neodymium.

5. The touchscreen cover of claim 4, wherein said activator comprises ytterbium and is chosen from ytterbium/erbium, ytterbium/thulium, ytterbium/terbium, and ytterbium/holmium.

6. The touchscreen cover of claim 1, wherein the initial electromagnetic radiation (A) comprises infrared radiation or visible light.

7. The touchscreen cover of claim 1, wherein said at least one phosphor has an average particle size ranging from 5 nm to 1000 nm.

8. The touchscreen cover of claim 1, wherein said at least one phosphor is present in an amount ranging from 0.01% to 60% by weight, relative to the total weight of the composition.

9. The touchscreen cover of claim 1, wherein said plastic resin comprises a polymer or co-polymer of polyvinyl chloride (PVC), polyethylene terephthalate (PET), polymethylmethacrylate (PMMA), polycarbonate (PC), acrylonitrile butadiene styrene (ABS), olefin, styrene, nylon, and acetal.

10. The touchscreen cover of claim 1, further comprising an optically clear adhesive material attached to the bottom side of the touchscreen cover for attaching the touchscreen cover to the touchscreen.

11. The touchscreen cover of claim 1, wherein the touchscreen cover is configured to couple to a smart phone, tablet, personal computer, point-of-sale (POS) system, kiosks, digital appliance, automated teller machines (ATMs).

12. The touchscreen cover of claim 1, further comprising an outer layer that is transparent or translucent to said initial electromagnetic energy (A).

13. The touchscreen cover of claim 12, wherein the outer layer comprises at least one coating on at least one surface that is transparent or translucent to an initial energy but that prevents UV radiation from exiting the touchscreen cover.

14. The touchscreen cover of claim 13, wherein said at least one coating comprises a metal or oxide chosen from MgO, TiO2, SiO2 and Al2O3.

* * * * *